United States Patent [19]

Hesse

[11] Patent Number: Plant 6,390

[45] Date of Patent: Nov. 15, 1988

[54] KALANCHOE PLANT NAMED ROSARITA

[75] Inventor: Peter S. Hesse, Bradenton, Fla.

[73] Assignee: Ball Pan Am Plant Co., Parrish, Fla.

[21] Appl. No.: 6,132

[22] Filed: Jan. 23, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Rosarita characterized by its rose pink flower color, compact growth habit, free branching and floriferous habit, early flower response, and by its adaptability to 10-15 cm pots.

1 Drawing Sheet

1

The present invention relates to a new and distinctive cultivar of Kalanchoe plant, botanically known as Kalanchoe, and referred to by the cultivar name Rosarita.

The new cultivar was referred to during the breeding and selection process by the designation K82-434H-P, and is a product of a planned breeding program. The basic objective of the breeding program was to create a new Kalanchoe cultivar having rose pink flowers, compact habit, short flowering response, and good keeping quality.

Rosarita was originated from a cross made in a controlled breeding program in Parrish, Fla. The female, or seed parent was the cultivar Sensation, (disclosed in U.S. Plant Pat. No. 4,727). The male, or pollen parent was the cultivar Firefly, disclosed in U.S. Plant Pat. No. 4,728.

Rosarita was discovered and selected by me as a flowering plant within the progeny of the stated cross in a controlled environment in Parrish, Fla. Asexual reproduction of the new cultivar by stem cuttings, as performed by me at Parrish, Fla., has demonstrated that the combination of characteristics as herein disclosed for the new cultivar are firmly fixed and are retained through successive generations of asexual reproduction.

Rosarita has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Rosarita, which in combination distinguish this Kalanchoe as a new and distinct cultivar:

1. Distinctive and pleasing rose pink flower color.
2. Compact habit and average growth rate.
3. Freely branching, with shoots formed at every node.
4. Suitable for production in 10-15 cm pots, and flowering in 12-14 weeks using photoperiodic control.
5. Very floriferous, with numerous flowers formed at every node.
6. Responds to B-9 applications to control height.
7. Medium sized leaves that are very thick and persistent.

The new cultivar is most similar to Sensation, with the Chart A attached hereto comparing important characteristics of each cultivar. Rosarita is principally distinguished from Sensation by its earlier flowering response, more compact habit, lighter pink color, and slightly larger leaves.

2

The accompanying photographic drawing shows a typical specimen plant of the new cultivar. The photograph is in black and white, with the true color of several flowers being illustrated.

In the following description, color references are made to The Royal Horticultural Society Colour Chart (R.H.S.), except where general colors of ordinary significance are referred to. Color values were taken under fluorescent light conditions in September in Parrish, Fla.

Botanical Classification: Kalanchoe, cv. Rosarita.

Parentage:

*Male parent.*—Firefly.

*Female parent.*—Sensation.

Propagation: The new cultivar holds its distinguishing characteristics through successive propagations by leaf cuttings and by division of shoots.

(A) *Type cutting.*—Shoot tip.

(B) *Time to root.*—Summer: 10-14 days at 21° C.

(C) *Rooting habit.*—Fibrous, many very fine roots.

Plant description:

(A) *Form.*—Upright, short compact habit; scheduling practices can produce small plants in 10 cm pots or larger plants in 15 cm pots.

(B) *Habit of growth.*—Average rate for this type of plant; shoots are formed at every node.

(C) *Foliage description.*—Leaves are simple, opposite and ovate with unevenly crenate margins. (1) Size: 5-15 cm long and 5-10 cm wide. (2) Shape: Ovate. (3) Texture: Smooth, waxy and succulent. (4) Margin: Unevenly crenate. (5) Color: Young and mature foliage top side 147A, under side 147B.

Flowering description:

(A) *Flowering habit.*—Compound dichasial cyme on strong peduncles. Peduncle length depends on growing conditions and B-9 applications. Pedicles up to 7 mm long.

(B) *Natural flowering season.*—Fall. Flowering time under controlled day length at 70°-85° F. in summer is 14 weeks; in winter at 62°-70° F., 12 weeks. Flowering time depends on temperature, light intensity and other growing conditions.

(C) *Flower buds.*—Oblong, developing to tubular as petals mature. Sheathed with four green sepals. Corolla at maturity about 14–17 mm. (1) Size: 14–17 mm. (2) Shape: Oblong. (3) Rate of opening: Normal.

(D) *Flowers borne.*—Compound dichasial cyme on strong peduncles. Peduncle length depends on growing conditions and B-9 applications. Pedicles up to 7 mm long.

(E) *Quantity of flowers.*—Very floriferous with new buds continuing to develop.

(F) *Petals.*—(1) Shape: Corolla funnel shaped, petal apex abruptly acuminate. (2) Color: Top side when opening, 51A, fading to 51B; under side, 50D. (3) Number and size of petals: Four (4), petals 7 mm in diameter, total flower diameter 14–16 mm.

(G) *Reproductive organs.*—(1) Stamens: Eight (8) in number. (a) Anther shape: Flat, elliptical. (b) Filament color: Yellow. (c) Pollen color: Yellow. (2) Pistils (a) Stigma shape: Flat, crystalline. (b) Style color: Greenish-white. (c) Ovaries: 4-celled, 7 mm long, green.

Disease resistance: No known Kalanchoe diseases observed to date.

General Observations: Rosarita is characterized by its rose pink flower color, compact and freely branching habit, and medium green foliage. Rosarita has an average 12–14 week flowering response and is adaptable to production in 10–15 cm pots year round.

CHART A

| | Rosarita vs. Sensation Summer Conditions | |
|---|---|---|
| | Rosarita | Sensation |
| Mature flower color | 51B | 58B (White Eye) |
| Flowering plant height | 17 cm | 21 cm |
| Weeks to flower | 13 | 14 |
| Mature leaf width | 8 cm | 6 cm |
| Mature leaf length | Up to 14 cm | Up to 12 cm |
| Diameter of Flower | 15 mm | 15 mm |

The plants of Rosita and Sensation which were used in this comparison were grown together on the same bench in a greenhouse in Parrish, Florida. The color readings were taken under fluorescent light at 2:00 pm on September 17, 1986.

I claim:

1. A new and distinct cultivar of Kalanchoe plant named Rosarita, as described and illustrated, and particularly characterized by its rose pink flower color, compact growth habit, free branching and floriferous habit, early flower response, and by its adaptability to 10–15 cm pots.

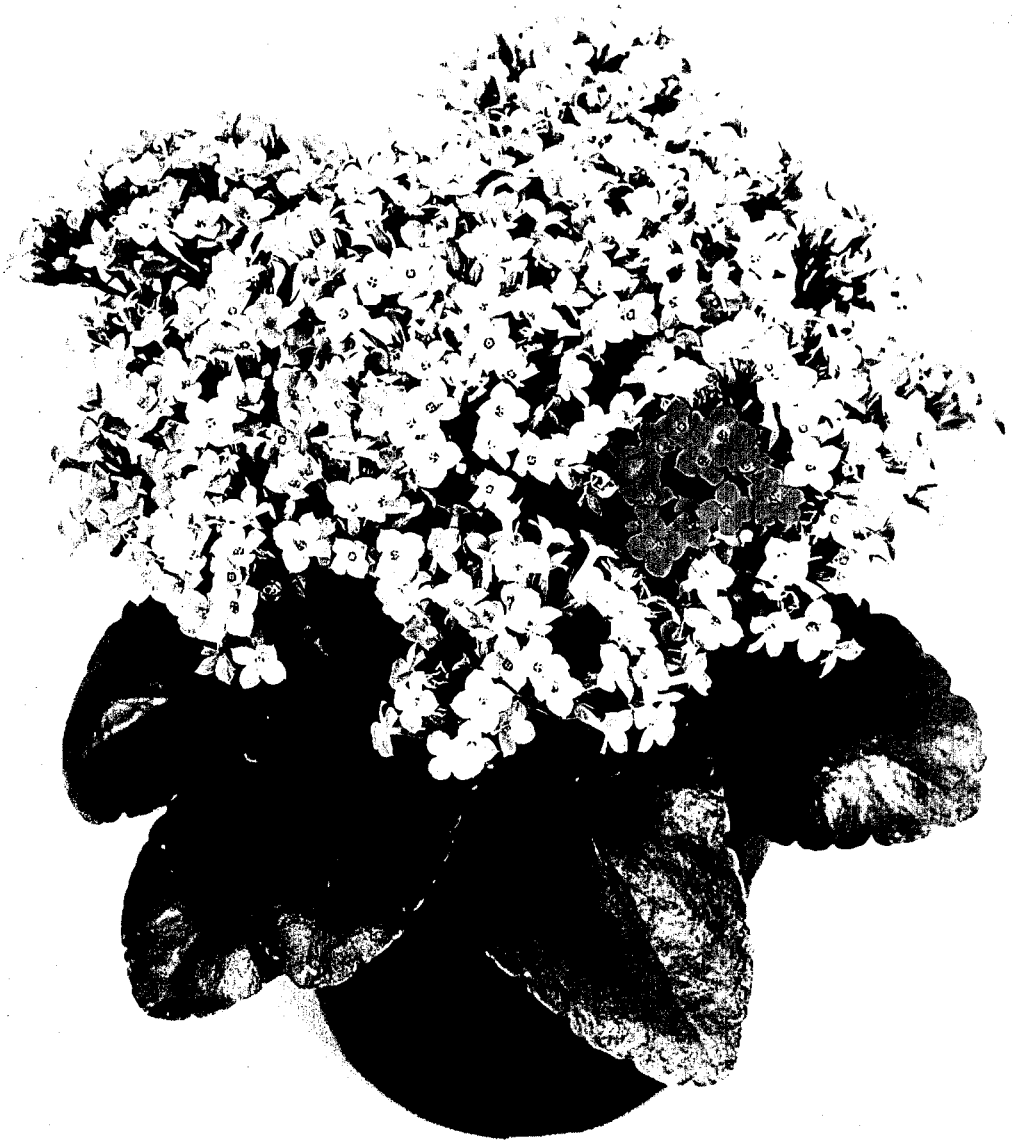

* * * * *